United States Patent [19]
Zwiener et al.

[11] Patent Number: 5,334,637
[45] Date of Patent: Aug. 2, 1994

[54] ISOCYANATOCARBOXYLIC ACIDS, A PROCESS FOR THEIR PREPARATION AND THEIR USE IN COATING COMPOSITIONS AS CROSS-LINKING AGENTS

[75] Inventors: Christian Zwiener, Cologne, Fed. Rep. of Germany; Rainer Rettig, Nishinomiya, Japan; Klaus Nachtkamp, Duesseldorf, Fed. Rep. of Germany; Josef Pedain, Cologne, Fed. Rep. of Germany; Dieter Arlt, Cologne, Fed. Rep. of Germany

[73] Assignee: Bayer Aktiengesellschaft, Leverkusen, Fed. Rep. of Germany

[21] Appl. No.: 988,663

[22] Filed: Dec. 10, 1992

[30] Foreign Application Priority Data

Dec. 20, 1991 [DE] Fed. Rep. of Germany ....... 4142275

[51] Int. Cl.⁵ .................. C08J 3/00; C08K 3/20; C08L 51/00; C08L 75/00
[52] U.S. Cl. .................................... 524/539; 524/591; 524/839; 524/840; 528/44; 528/65; 528/85
[58] Field of Search ............... 524/539, 591, 840, 839; 528/44, 65, 85

[56] References Cited

U.S. PATENT DOCUMENTS

| | | | |
|---|---|---|---|
| 3,829,587 | 8/1974 | Tolstoguzov et al. | 426/350 |
| 3,959,348 | 5/1976 | Reiff et al. | 260/471 |
| 4,186,118 | 1/1980 | Reischl et al. | 260/29.2 TN |
| 4,408,008 | 10/1983 | Markusch | 528/68 |
| 4,433,095 | 2/1984 | Hombach et al. | 524/563 |
| 4,613,685 | 9/1986 | Klein et al. | 560/330 |
| 4,663,377 | 5/1987 | Hombach et al. | 524/196 |
| 4,711,918 | 12/1987 | Kubitza et al. | 524/196 |
| 4,835,239 | 5/1989 | Klein et al. | 528/44 |
| 5,098,947 | 3/1992 | Metzger et al. | 524/507 |
| 5,098,983 | 3/1992 | Mosbach et al. | 528/59 |
| 5,202,377 | 4/1993 | Thorne et al. | 524/591 |

FOREIGN PATENT DOCUMENTS

| | | |
|---|---|---|
| 3608354 | 9/1987 | Fed. Rep. of Germany . |
| 3620821 | 12/1987 | Fed. Rep. of Germany . |
| 969550 | 12/1950 | France . |

Primary Examiner—Paul R. Michl
Assistant Examiner—P. Niland
Attorney, Agent, or Firm—Joseph C. Gil; Thomas W. Roy; Richard E. L. Henderson

[57] ABSTRACT

The present invention relates to isocyanatocarboxylic acids containing
a) 1 to 30% by weight of isocyanate groups attached to (cyclo)aliphatic tertiary carbon atoms and
b) 0.5 to 500 milliequivalents, per 100 g of isocyanatocarboxylic acids, of carboxyl groups which may be at least partially present in carboxylate salt form.

The present invention also relates to a process for the preparation of these isocyanatocarboxylic acids and to their use as cross-linking agents for aqueous coating compositions.

7 Claims, No Drawings

ISOCYANATOCARBOXYLIC ACIDS, A PROCESS FOR THEIR PREPARATION AND THEIR USE IN COATING COMPOSITIONS AS CROSS-LINKING AGENTS

BACKGROUND OF THE INVENTION

1. Field of the Invention

This invention relates to new, storage stable isocyanatocarboxylic acids wherein the isocyanate groups are attached to tertiary carbon atoms and carboxyl groups which may be at least partially present in carboxylate salt form, to a process for their preparation and to their use as cross-linking agents for aqueous coating compositions.

2. Description of the Prior Art

The importance of aqueous lacquers and coating compositions has increased in recent years due to the ever stricter emission guidelines concerning solvents released in the application of lacquers. Although aqueous coating compositions are now available for many fields of application, in many cases they can only attain the high level of quality of conventional, solvent-containing coating compositions with regard to their resistance to solvents and chemicals and to mechanical attack if they are subjected to a chemical cross-linking during film formation.

Only a few attempts have previously been made to achieve a cross-linking of aqueous coating compositions by means of compounds containing free isocyanate groups, i.e., to apply the concept of reactive polyurethane coating compositions which has proved satisfactory in the field of solvent-containing coating compositions to aqueous systems.

DE-OS 2,708,442 describes the addition of monomeric organic diisocyanates for improving the properties of aqueous polyurethane dispersions.

According to DE-OS 3,529,249 organic polyisocyanates may be used for increasing the resistance to solvents and chemicals and improving the wear resistance of coatings based on homo and copolymers dispersed in water. The described positive effects on the coating properties may be attributed to the formation of a "shell of urea" around the dispersed polymer particles resulting from a reaction of the isocyanates with water. Therefore, the polyisocyanates used as additives do not act as cross-linking agents for aqueous dispersions of synthetic resins or synthetic resin precursors containing isocyanate reactive groups.

The preparation of an aqueous polyurethane reactive system from selected aqueous polyhydroxyl compounds which have an emulsifying action and low viscosity free polyisocyanates is the disclosed in DE-OS 3,829,587. The properties of the coatings obtained are equal to those of conventional solvent-containing, two-component lacquers. The process is, however, limited to special polyol dispersions due to the generally poor dispersibility of organic polyisocyanates in water. To apply this method to any aqueous binders containing isocyanate reactive groups would require hydrophilically modified, self-dispersible polyisocyanate components.

Aromatic, hydrophilically modified polyisocyanates such as those described, e.g., in DE-OS 2,359,613 and EP-A-61,628, are not suitable for use in aqueous coating compositions due to their high reactivity with water and consequent evolution of carbon dioxide. They are preferentially used for the production of foams and in the field of adhesives. Isocyanate-functional, cross-linking agents for aqueous coating systems can only be prepared using less reactive (cyclo)aliphatic polyisocyanates.

Hydrophilically modified aliphatic polyisocyanates are described as additives for aqueous adhesives in EPA-0,206,059. These polyisocyanates are rendered emulsifiable by the incorporation of polyether chains containing ethylene oxide units. Such hydrophilicised polyisocyanates are, however, less suitable for use in the field of lacquers because the coatings remain hydrophilic on account of the relatively high polyether content.

Polyisocyanate mixtures containing carboxyl groups and containing uretdione groups as an essential feature of the invention are described in DE-OS 4,001,783. These products are used inter alia as binders for coating compositions. Since preparation of the polyisocyanates containing uretdione groups requires a separate process step, namely the dimerization of the starting isocyanates, this is a relatively complicated process. Another disadvantage common to basically all processes for the preparation of products containing isocyanate groups from the diisocyanates known in polyurethane chemistry, such as hexamethylene diisocyanate and isophorone diisocyanate, is that after these products have been prepared, they have a residual monomer content which is too high for the required standards of work hygiene and must subsequently be removed by expensive processes, e.g., thin layer distillation.

Therefore, it is an object of the present invention to provide compounds which 1) contain both isocyanate groups and carboxyl groups, 2) are storage stable, i.e., undergo no significant amount of reaction between the isocyanate groups during storage, 3) are soluble or dispersible in water after neutralization with bases and 4) have a pot life of several hours in the aqueous phase and are suitable for cross-linking aqueous coating compositions. Further, the process for the preparation of these compounds should result in products containing less than 2% by weight of monomeric diisocyanates without requiring an expensive after-treatment.

These objects may be achieved with the isocyanatocarboxylic acids according to the present invention which are described below and the process for their preparation.

SUMMARY OF THE INVENTION

The present invention relates to isocyanatocarboxylic acids containing a) 1 to 30% by weight of isocyanate groups attached to (cyclo)aliphatic tertiary carbon atoms and b) 0.5 to 500 milliequivalents, per 100 g of isocyanatocarboxylic acids, of carboxyl groups which may be at least partially present in carboxylate salt form.

The present invention also relates to a process for the preparation of these isocyanatocarboxylic acids by reacting at an NCO/OH equivalent ratio of 1:6:1 to 2:1

A) a diisocyanate having a molecular weight of 168 to 300, an isocyanate group attached to a primary aliphatic carbon atom and an isocyanate group attached to a tertiary (cyclo)aliphatic carbon atom and B) up to 25 isocyanate equivalents percent, based on the equivalents of components A) and B), of one or more diisocyanates other than those set forth in A) which have a molecular weight of 168 to 300 and contain (cyclo)aliphatically bound isocyanate groups with C) 2,2-bis-(hydroxymethyl)-alkanoic acids corresponding to the formula

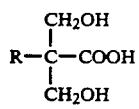

wherein
R represents hydrogen, a hydroxymethyl group or an alkyl group having 1 to 20 carbon atoms and D) optionally one or more organic polyhydroxyl compounds other than those set forth in C).

Finally, the present invention relates to aqueous coating compositions containing the isocyanatocarboxylic acids as cross-linking agents and an aqueous dispersion or aqueous solution of a resin which is reactive with isocyanate groups.

DETAILED DESCRIPTION OF THE INVENTION

Diisocyanates A) may be any diisocyanates having a molecular weight of 168 to 300, an isocyanate group attached to a tertiary (cyclo)aliphatic carbon atom and an isocyanate group attached to a primary aliphatic carbon atom. Suitable diisocyanates include those corresponding to the formula:

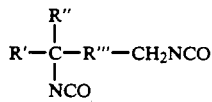

wherein
R' and R" may be the same or different and represent alkyl groups having 1 to 4 carbon atoms and R'" represents a divalent, optionally branched, saturated aliphatic hydrocarbon group having 2 to 9 carbon atoms.

Examples of these diisocyanates and a process for their preparation are described, for example, in DE-OS 3,608,354 and DE-OS 3,620,821. Preferred diisocyanates are those wherein R' and R" both represent methyl groups and R'" represents a divalent linear aliphatic hydrocarbon group having 2 to 5 carbon atoms.

Examples of these diisocyanates include 1,4-diisocyanato-4-methylpentane, 1,5-diisocyanato-5-methylhexane, 1,6-diisocyanato-6-methylheptane, 1,5-diisocyanato-2,2,5-trimethylhexane and 1,7-diisocyanato-3,7-dimethyloctane.

The compounds used as starting component A) are preferably aliphatic-cycloaliphatic diisocyanates corresponding to the formula

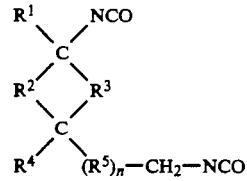

wherein
$R^1$ represents an alkyl group having 1 to 4 carbon atoms, preferably a methyl group, $R^2$ and $R^3$ may be the same or different and represent divalent, saturated aliphatic hydrocarbon groups having 1 to 4 carbon atoms, preferably 1 to 3 carbon atoms, wherein the sum of the carbon atoms in these groups is preferably 3 to 6, more preferably 4 or 5, $R^4$ represents hydrogen or for an alkyl group having 1 to 4 carbon atoms, preferably hydrogen or a methyl group, $R^5$ represents a divalent saturated aliphatic hydrocarbon group having 1 to 4, preferably 1 to 3 carbon atoms and n represents 0 or 1.

Examples of these aliphatic-cycloaliphatic diisocyanates include 1-isocyanato-1-methyl-4(3)-isocyanatomethyl-cyclohexane (which is generally present as a mixture of the 4- and 3-isocyanatomethyl isomers), 1-isocyanato-1-methyl-4-(4-isocyanatobut-2-yl)-cyclohexane, 1-isocyanato-1,2,2-trimethyl-3-(2-isocyanatoethyl)-cyclopentane and 1-isocyanato-1,4(3)-dimethyl-4(3)-isocyanatomethyl-cyclohexane (which is generally present as a mixture of the 4-methyl-4-isocyanatomethyl and 3-methyl-3-isocyanatomethyl isomers. 1-isocyanato- 1-n-butyl-3-(4-isocyanatobut-1-yl)-cyclohexane and 1-isocyanato-1,2-dimethyl-3-ethyl-3-isocyanatomethylcyclopentane.

The preparation of these aliphatic-cycloaliphatic diisocyanates is described, for example, in EP-A-0,153,561. Mixtures of the aliphatic cycloaliphatic diisocyanates corresponding to the formula may also be used as component A) in the process according to the invention.

The diisocyanates A) may be used together with other diisocyanates B) in an amount of up to 25 NCO equivalent percent, based on the total quantity of diisocyanates A) and B).

The optional diisocyanates B) are selected from diisocyanates having a molecular weight of 168 to 300 which have aliphatically and/or cycloaliphatically bound isocyanate groups and do not contain isocyanate groups attached to tertiary carbon atoms. Examples of these diisocyanates include hexamethylene diisocyanate, 1-isocyanato-3,3,5-trimethyl-5-isocyanatomethyl cyclohexane and/or 4,4'-diisocyanatodicyclohexylmethane. The inclusion of diisocyanates B) is not preferred.

Component C) is selected from 2,2-bis-(hydroxymethyl)alkanoic acids corresponding to the formula

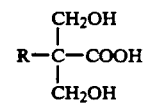

wherein
R represents hydrogen, a hydroxymethyl group or an alkyl group having up to 20 carbon atoms, preferably up to 8 carbon atoms.

Preferred acids include 2,2-bis-(hydroxymethyl)-acetic acid, 2,2,2-tris-(hydroxymethyl)-acetic acid, 2,2-bis-(hydroxymethyl)-butanoic acid and 2,2-bis-(hydroxymethyl)-pentanoic acid. Especially preferred is 2,2-bis-(hydroxymethyl)propionic acid.

Optional component D) is selected from low molecular weight aliphatic polyols D1) having a molecular weight of 62 to 799; relatively high molecular weight polyhydroxyl compounds D2) having a molecular weight ($M_n$, determined by vapor pressure or membrane osmometry) of 800 to 12,000, preferably 800 to 5000; and/or mono- or polyhydric alcohols D3) containing hydrophilic groups. Among these hydroxyl group-containing compounds D), the low molecular weight, polyhydric alcohols D1) are preferred.

The low molecular weight polyhydric alcohols are preferably aliphatic polyols having a molecular weight of 62 to 799, preferably 62 to 200. Examples of these alcohols include ethanediol, 1,2- and 1,3-propanediol, 1,3-, 2,3- and 1,4-butanediol, 1,6-hexanediol, 1,8-octanediol, neopentyl glycol, 1,4-bis-(hydroxymethyl )-cyclohexane, 2-methyl-1,3-propanediol, 2,2,4-trimethyl-1,3-pentanediol, 2-ethyl-1,3-hexanediol, perhydrobisphenol A, glycerol, trimethylolpropane, 1,2,6-hexanetriol; low molecular weight hydroxyl group-containing esters prepared from these polyols and the dicarboxylic acids to be described hereinafter; low molecular weight ethoxylation and/or propoxylation products of these alcohols; and mixtures of any of the preceding modified or unmodified alcohols.

The relatively high molecular weight polyhydroxyl compounds D2) are known from polyurethane chemistry. These polyhydroxyl compounds have at least two hydroxyl groups per molecule and preferably have a hydroxyl group content of 0.3 to 17% by weight, more preferably 0.9 to 6% by weight.

Relatively high molecular weight polyhydroxyl compounds include polyester polyols which are prepared from the previously described monomeric alcohols and polybasic carboxylic acids such as adipic acid, sebacic acid, phthalic acid, isophthalic acid, tetrahydrophthalic acid, hexahydrophthalic acid, maleic acid, the anhydrides of these acids and any mixtures of these acids or acid anhydrides. Hydroxyl group-containing polylactones are also suitable, in particular poly-$\epsilon$-caprolactones.

Also suitable for use as component D2) are polyether polyols obtained in known manner by the alkoxylation of suitable starter molecules such as the previously described monomeric polyols, water, organic polyamines having at least two NH bonds and mixtures thereof. Ethylene oxide and/or propylene oxide are particularly suitable alkylene oxides for the alkoxylation reaction wherein the alkylene oxides may be added as mixtures or sequentially.

Polycarbonates containing hydroxyl groups are also suitable as component D2), e.g., polycarbonates obtained by the reaction of the previously described monomeric diols with phosgene or diarylcarbonates such as diphenylcarbonate.

The known polyhydroxy polyacrylates may also be used as component D2). These compounds are copolymers of olefinic monomers containing hydroxyl groups with olefinic monomers which are free from hydroxyl groups. Examples of suitable monomers include vinyl and vinyl idene monomers such as styrene, $\alpha$-methylstyrene, o- and p-chlorostyrene, o-, m- and p-methylstyrene and p-tert.-butylstyrene; acrylic acid; (meth)acrylonitrile; acrylic and methacrylic acid esters having 1 to 8 carbon atoms in the alcohol component such as ethyl acrylate, methyl acrylate, n- and isopropyl acrylate, n-butyl acrylate, 2-ethylhexyl acrylate, 2-ethylhexyl methacrylate, isooctyl acrylate, methyl methacrylate, ethyl methacrylate, butyl methacrylate and isooctyl methacrylate; diesters of fumaric acid, itaconic acid or maleic acid having 4 to 8 carbon atoms in the alcohol component; (meth)acrylic acid amide; vinyl esters of alkane monocarboxylic acids having 2 to 5 carbon atoms such as vinyl acetate or vinyl propionate; and hydroxyalkyl esters of acrylic acid or methacrylic acid having 2 to 4 carbon atoms in the hydroxyalkyl group such as 2-hydroxyethyl, 2-hydroxypropyl, 4-hydroxybutyl and trimethylolpropane mono- or pentaerythritol monoacrylate or monomethacrylate. Mixtures of these monomers may also be used for the preparation of the hydroxy-functional polyacrylates.

Examples of suitable hydroxyl compounds D3) include diols having hydrophilic side chains such as those described in U.S. Pat. No. 4,190,566 and hydrophilic monohydric polyether alcohols such as those described in U.S. Pat. No. 4,237,264. Other polyol components containing hydrophilic or potential hydrophilic groups such as sulphonate groups may also be used as component D3) or a portion of component D3).

The isocyanatocarboxylic acids according to the invention contain 1 to 30% by weight, preferably 2 to 20% by weight, of isocyanate groups attached to (cyclo)aliphatic tertiary carbon atoms and 0.5 to 500, preferably 5.0 to 300 and more preferably 10 to 100 milliequivalents of carboxyl groups, per 100 g of solids content. A portion of the carboxyl groups may optionally be in neutralized salt form. The isocyanate functionality of the compounds according to the invention is generally at least 2.0, preferably 2.0 to 4.5. The amount of ethylene oxide units ($CH_2$—$CH_2$—O) incorporated in polyether chains in the isocyanatocarboxylic acids is 0 to 30%, preferably 0 to 20% and more preferably 0%. The compounds according to the invention may contain such polyether chains when a component D3) containing such chains has been used for carrying out the process according to the invention.

When carrying out the process according to the invention, the starting components A) and C) and optionally starting components B) and optionally D) are used in quantities which provide an equivalent ratio of isocyanate groups to hydroxyl groups of 1.4:1 to 2:1, preferably 1.6:1 to 2:1, provided that when diisocyanates B) which do not contain tertiary isocyanate groups are used, the equivalent ratio, based on the non-tertiary isocyanate groups of components A) and B) and the hydroxyl groups of components C) and D) is at most 1:1. The nature and quantitative ratios of the starting components are otherwise chosen so that the products obtained from the process are isocyanatocarboxylic acids having the properties previously described.

The process according to the invention may be carried out either solvent-free or in the presence of inert solvents. It is preferably carried out in the presence of solvents which are inert towards isocyanate groups and these solvents are preferably used in quantities of up to 50% by weight, most preferably up to 40% by weight, based on the solution. Examples of suitable inert solvents include ethyl acetate, butyl acetate, ethylene glycol monomethyl and monoethyl ether acetate, butyl diglycol acetate, diethylene glycol dimethylether, 1-methoxypropyl-2-acetate, 2-butanone and mixtures of these solvents.

The process according to the invention may be carried out, for example, by introducing all of the starting components into the reaction vessel together or by first introducing diisocyanates A) and optionally B) together with component C) and homogeneously stirring the mixture. Component D) may then optionally be added, if necessary in the molten state, through a dropping funnel. The reaction temperature is maintained at 20° to 150° C., preferably 40° to 120° C. and more preferably 40° to 100° C. The reaction is terminated when the isocyanate content is equal to or slightly below the theoretical content calculated from the stoichiometry of the starting materials.

The residual monomer content of the products according to the invention thus obtained is generally below 2% by weight, preferably below 1% by weight, without a separate step having been carried out to remove the monomers. If diisocyanates B) which do not contain tertiary isocyanate groups have been used in the process described above, they are incorporated in the products of the process to an extent of at least 99.9% so that the end products generally contain less than 0.1% by weight of free, unbound diisocyanates B).

The isocyanatocarboxylic acids according to the invention may be obtained in a solvent-free form which may be liquid or solid, depending on the composition. The melting points of the solid compounds may be up to 200° C. The aggregate state and the melting point of the solvent-free products can be influenced by the choice of starting materials and their stoichiometric ratios.

The isocyanatocarboxylic acids are storage stable compounds at ambient temperature, i.e., no reaction takes place to any significant extent between the tertiary isocyanate groups and the carboxyl groups even during prolonged storage, i.e., a period of at least a year.

The isocyanatocarboxylic acids according to the invention are valuable precursors for the synthesis of high molecular weight polyurethanes from an aqueous medium. This synthesis may be carried out by, for example, blending hydroxyl group-containing polymers or semipolymers dissolved or dispersed in water with the at least partially neutralized isocyanatocarboxylic acids, which may be dissolved or dispersed in water, to form aqueous two-component systems. The two-component systems are subsequently reacted on a substrate to provide coatings.

It is particularly preferred to use the isocyanatocarboxylic acids according to the invention in an at least partially neutralized form as cross-linking agents for aqueous coating compositions containing aqueous solutions and/or dispersions of synthetic resins or synthetic resin precursors as binders.

Both applications require an at least partial conversion of the carboxyl groups into the salt form by neutralization with a suitable base to ensure solubility or dispersibility of the isocyanatocarboxylic acids in water. Tertiary amines such as triethylamine, N-methylpyrrolidine, N-methylpiperidine and N-methylmorpholine, and isocyanate-reactive tertiary amines, in particular amino alcohols such as triethanolamine, N-methyldiethanolamine, 2-(N,N-dimethylamino)-isopropanol or N,N-dimethyiethanolamine are particularly suitable bases.

The at least partial neutralization of the carboxyl groups is generally carried out after the addition reaction according to the invention although it is also possible use at least partially neutralized starting components C) as the starting material for the preparation of the isocyanatocarboxylic acids.

If the isocyanatocarboxylic acids are present in liquid form, either solvent-free or as solutions, they may be stirred into the water containing the chosen quantity of amine or the water containing amine may be stirred into the liquid polyisocyanatocarboxylic acids. The liquid isocyanatocarboxylic acids may also initially be partly or completely neutralized with the amine and then introduced into the water or the water may be introduced into the neutralized isocyanatocarboxylic acids. If the isocyanatocarboxylic acids according to the invention are in solid form, they are most suitably ground before they are stirred into water containing the desired quantity of neutralizing amine.

Whether these procedures result in solutions or dispersions of the isocyanatocarboxylic acids according to the invention depends upon the nature and quantitative ratios of the starting materials used for their preparation and, in particular, on the amount of hydrophilic groups. One of the most important properties of the isocyanatocarboxylic acids according to the invention is that they remain substantially unaltered in the aqueous medium for an extended period since the tertiary isocyanate groups react very slowly with water. The aqueous solutions or dispersions containing the isocyanatocarboxylic acids according to the invention generally have a pot life of several hours.

The isocyanatocarboxylic acids according to the invention and the aqueous coating binders which are to be cross-linked may be combined with one another, e.g., by simply stirring together the aqueous solutions or dispersions of the isocyanatocarboxylic acids according to the invention and the aqueous lacquer or coating binders which are to be cross-linked.

Alternatively, the isocyanatocarboxylic acids according to the invention may be stirred into the aqueous coating binder to be cross-linked, which contains the chosen amine for neutralization and optionally a further quantity of water. Aqueous coating compositions suitable for cross-linking with the isocyanatocarboxylic acids according to the invention include in particular those containing, as binders, synthetic resins or synthetic resin precursors selected from {i}polyurethanes dispersed in water which can be cross-linked with polyisocyanates by virtue of the active hydrogen atoms present in the urethane groups; (ii) hydroxyl group-containing polyacrylates dissolved or dispersed in water, in particular those having a molecular weight of 1000 to 10,000, which are valuable two-component binders when used in combination with organic polyisocyanates as cross-linking agents and (iii) hydroxyl group-containing, optionally urethane-modified polyester resins dispersed in water, which are known from the chemistry of polyesters and alkyd resins.

The usual auxiliary agents and additives may also be added to the coating systems formulated with the isocyanatocarboxylic acids according to the invention.

The two-component aqueous coating compositions may be applied in one or more layers to any substrate by known methods, e.g., by spraying, brush coating, immersion or flooding or by means of rollers or coating knives.

The examples given below serve to illustrate the invention in more detail. All parts and percentages are by weight unless otherwise specified.

Starting Components A

Diisocyanate I 1-isocyanato-1-methyl-4(3)-isocyanatomethylcyclohexane (Example 1 of DE-OS 3,402,623, U.S. Pat. No. 4,613,685)

Diisocyanate II 1-isocyanato-1-methyl-4-(4-isocyanatobut-2-yl)-cyclohexane (Example 2 of DE-OS 3,402,623, U.S. Pat. No. 4,613,685)

Starting Components D

Polyester I

A polyester having an average molecular weight of 840 and prepared from adipic acid and 1,6-hexanediol. Hydroxyl group content: 4%

Polyether I

A linear, monohydroxy ethylene oxide/propylene oxide mixed ether started on diethylenglycol-mono-n-butylether ("butyldiglycol").
Molecular weight: about 2250
Hydroxyl group content: 0.75%

Polyether II

A dihydroxy, ethylene oxide/propylene oxide mixed ether (Tegomer D-3123, available from Th. Goldschmidt AG, Essen).
Molecular weight: about 1180
Hydroxyl group content: 2.9%

Dispersion I

An aqueous polyester dispersion which has a solids content of 55% and an OH number of about 40, and was prepared from
7.5 % trimethylolpropane
15.4 % hexane-1,6-diol
26.4 % phthalic acid anhydride
5.6 % tetrahydrophthalic acid anhydride
3.8 % dimethylethanolamine
14.7 % butyl glycol
6.7 % i-butanol
19.8 % water

Dispersion II

An aqueous polyester dispersion which has a solids content of 67% and an OH number of about 67, and was prepared from 25.4 % hexane-1,6-diol
6.7 % trimethylolpropane
27.8 % phthalic acid anhydride
7.1% trimellitic acid anhydride
13.3 % butyl diglycol
5.2 % dimethylethanolamine
14.5 % water

Dispersion III

An aqueous dispersion of a hydroxyl group-containing polyester-polyurethane resin which has a solids content of 46.5% and an OH number of about 33, and was prepared from
1.2 % isononanoic acid
5.8 % trimethylolpropane
7.2 % hexane-1,6-diol
4.0 % cyclohexanedimethanol
7.4 % adipic acid
8.4 % isophthalic acid
2.9 % dimethylolpropionic acid
9.3 % isophorone diisocyanate
1.2 % dimethylethanolamine
0.4 % levelling agent (Additol XW 395, Hoechst AG, Frankfurt)
52.2 % water

Dispersion IV

An aqueous dispersion of a polyacrylate which has a solids content of 45% and an OH number of about 60, and was prepared from
14.0 % hydroxyethylmethacrylate
8.0 % methyl methacrylate
18.3 % butyl acrylate
3.7 % acrylic acid
1.5 % azoisobutyric acid nitrile
0.3 % t-butyloctoate
2.0 % ammonia
52.2 % water

Dispersion V

An aqueous dispersion of a polyester polyurethane which has a solids content of 45% and an OH number of about 33, and was prepared from
2.0 % soya oil fatty acid
5.6 % trimethylolpropane
10.1% hexane-1,6-diol
7.1% adipic acid
8.1% isophthalic acid
2.8 % dimethylolpropionic acid
9.2 % isophorone diisocyanate
0.1% tin(II)octoate
1.3 % dimethylethanolamine
53.7 % water

Dispersion VI

An aqueous dispersion of a polyacrylate which has a solids content of 40% and an OH number of about 38, and was prepared from
11.2 % styrene
5.0 % methyl methacrylate
13.5 % butyl acrylate
6.8 % hydroxyethyl methacrylate
2.0 % acrylic acid
0.7 % dodecylmercaptan
0.3 % dimethylethanol amine
0.4 % emulsifier (3-benzyl-4-hydroxy-biphenylpolyglycolether)
0.1% ammonium peroxydisulphate
60.0 % water

EXAMPLES

Example 1

70.7 parts of Diisocyanate I and 29.3 parts of 2,2-bis-(hydroxymethyl)-propionic acid were introduced together into a reaction vessel and heated to about 80° C. The exothermic reaction which set in raised the temperature to about 130° C. When this reaction had died down, the temperature was maintained at about 100° C. for 6 hours.

A colorless solid having an isocyanate content of 7.6%, a carboxyl group content of 219 milliequivalents per 100 g and a melting point of 135° to 145° C. was obtained. The monomeric diisocyanate I content was 0.4%.

Example 2

33.2 parts of Diisocyanate I, 40.4 parts of Polyester I and 6.4 parts of 2,2-bis-(hydroxymethyl)-propionic acid were introduced into 20.0 parts of toluene. The reaction mixture was stirred for one hour at 50° C., then for 7 hours at 60° C. and then for a further 7 hours at 900C. After removal of the solvent by distillation, a colorless waxy product having an isocyanate content of 6.3% and a carboxyl group content of 60 milliequivalents per 100 g was obtained. The monomeric Diisocyanate I content was 1.4%.

Example 3

50.0 parts of Diisocyanate I, 6.9 parts of 2,2-bis-(hydroxymethyl)-propionic acid, 2,6 parts of ethylene glycol and 5.5 parts of trimethylolpropane were introduced into 35.0 parts of ethyl acetate. The mixture was left to react at 60° C. for 18 hours and a pale yellow solution having a viscosity of 1600 mPa.s (23° C.) was obtained. The isocyanate content was 12.3%, the carboxyl group content 79 milliequivalents per 100 g and the monomeric diisocyanate content was 1.1%, based in each case on the solids content.

The stability in storage at room temperature was tested by checking the isocyanate group content and the viscosity over an extended period.

| Time (Months) | Isocyanate content (%) | Viscosity (mPa.s 23° C.) |
| --- | --- | --- |
| 0 | 8.0 | 1600 |
| 2 | 7.8 | 1800 |
| 4 | 7.7 | 1950 |
| 6 | 7.7 | 2200 |
| 8 | 7.6 | 2300 |
| 10 | 7.5 | 2450 |
| 12 | 7.4 | 6600 |

Example 4

50.0 parts of Diisocyanate I and 6.9 parts of 2,2-bis-(hydroxymethyl)-propionic acid were introduced into 35.0 parts of butyl acetate. 2.6 parts of ethylene glycol and 5.5 parts of trimethylolpropane which had been melted were added together dropwise at 50° C. over a period of 2 hours. Stirring was then continued, first for 2 hours at the same temperature and then for 8 hours at 60° C. and 8 hours at 100° C. The pale yellow solution had a viscosity of 9300 mPa.s {23° C.). The isocyanatocarboxylic acid had an isocyanate content of 11.7%, a carboxyl group content of 79 milliequivalents per 100 g and a monomeric diisocyanate content of 0.2%, based in each case on the solids content.

Example 5

51.1 parts of Diisocyanate I and 7.1 parts of 2,2-bis-hydroxymethyl)-propionic acid were introduced into 30.0 parts of diethylene glycol dimethylether and heated to 50° C. 6.2 parts of 1,8-octanediol and 5.6 parts of 1,2,6-hexanetriol were added together dropwise in the molten state over a period of one hour. Stirring was then continued for 12 hours at 60° C. and 3 hours at 80° C. The solution obtained has a viscosity of 9500 mPa.s (23° C.).

The dissolved isocyanatocarboxylic acid had an isocyanate content of 11.7%, a carboxyl group content of 75 milliequivalents per 100 g and a monomeric diisocyanate content of 1.1%, based in each case on the solids content.

Example 6

36.0 parts of Diisocyanate I and 5.0 parts of 2,2-bis-hydroxymethyl)-propionic acid were introduced into 30.0 parts of diethylene glycol dimethylether. 25.0 parts of Polyester I and 4.0 parts of 1,2,6-hexanetriol were introduced together dropwise as a melt over a period of 2.5 hours at 50° C. The reaction mixture was then stirred for 9 hours at 60° C. and 3 hours at 80° C. The resulting solution had a viscosity of 8000 mPa.s (23° C.). The dissolved isocyanatocarboxylic acid had an isocyanate content of 8.4%, a carboxyl group content of 53 milliequivalents per 100 g and a monomeric diisocyanate content of 1.3%, based in each case on the solids content.

Example 7

48.5 parts of diisocyanate I were introduced into 35.0 parts of ethyl acetate. A mixture of 5.1 parts of 2,2,4-trimethyl-1, 3-pentanediol and 4.7 parts of trimethylolpropane was added dropwise at 60° C. over a period of 4 hours. The reaction mixture was then stirred at 60° C. for 10 hours and 6.7 parts of 2,2-bis-(hydroxymethyl)-propionic acid were added. A clear, pale yellow solution having a viscosity of 900 mPa.s (23° C.) was obtained after a further 18 hours at 60° C. and 8 hours at 80° C. The dissolved isocyanatocarboxylic acid had an isocyanate content of 13.9%, a carboxyl group content of 77 milliequivalents per 100 g and a monomeric diisocyanate content of 1.5%, based in each case on the solids content.

Example 8

52.5 parts of Diisocyanate I and 3.6 parts of 2,2-bis-(hydroxymethyl)-propionic acid were introduced into 30 parts of diethylene glycol dimethylether. 10.8 parts of 1,2,6-hexanetriol and 3.1 parts of Polyether I were added together dropwise at 55° C. over a period of 3 hours. The reaction mixture was then stirred for 12 hours at that temperature and for 8 hours at 80° C. The clear solution had a viscosity of 1600 mPa.s (23° C). The dissolved isocyanatocarboxylic acid had an isocyanate content of 14.3%, a carboxyl group content of 39 milliequivalents per 100 g and a monomeric diisocyanate content of 1.7%, based in each case on the solids content.

Example 9

38.5 parts of Diisocyanate I and 2.7 parts of 2,2-bis-(hydroxymethyl)-propionic acid were introduced into 30.0 parts of diethylene glycol dimethylether. 22.3 parts of Polyether I, 4.0 parts of trimethylolpropane and 2.5 parts of ethylene glycol were added dropwise over a period of 8 hours at 55° C. The reaction mixture was then stirred at that temperature for 12 hours and at 100° C. for 12 hours. The solution obtained had a viscosity of 350 mPa.s (23° C.). The dissolved isocyanatocarboxylic acid had an isocyanate content of 10.3%, a carboxyl group content of 28 milliequivalents per 100 g and a monomeric diisocyanate content of 1.8%, based in each case on the solids content.

Example 10

48.6 parts of Diisocyanate I and 3.4 parts of 2,2-bis-(hydroxymethyl)-propionic acid were introduced into 30.0 parts of diethylene glycol dimethylether. 10.7 parts of 1,2,6-hexanetriol and 7.4 parts of Polyether II were together added dropwise over a period of 6 hours at 55° C. The reaction mixture was then stirred for 8 hours at 60° C, for 8 hours at 80° C. and for 8 hours at 100° C. The clear yellow solution had a viscosity of 6,800 mPa.s (23° C.). The dissolved isocyanatocarboxylic acid had an isocyanate content of 10.9%, a carboxyl group content of 36 milliequivalents per 100 g and a monomeric diisocyanate content of 0.9%, based in each case on the solids content.

Example 11

37.5 parts of Diisocyanate I and 2.6 parts of 2,2-bis-(hydroxymethyl)-propionic acid were introduced into 30.0 parts of diethylene glycol dimethylether. 21.7 parts of Polyether I and 8.2 parts of trimethylolpropane were added together dropwise at 60° C. over a period of 6 hours. An isocyanate content of 6.0% was obtained after a further 12 hours at 60° C. and 12 hours at 100° C. The viscosity of the solution was 1500 mPa.s (23° C.). The dissolved isocyanatocarboxylic acid had an isocyanate content of 8.6%, a carboxyl group content of 28 milliequivalents per 100 g and a monomeric diisocyanate content of 1.3%, based in each case on the solids content.

Example 12

46.3 parts of Diisocyanate I, 8.0 parts of hexamethylene diisocyanate and 6.4 parts of 2,2-bis-{hydroxymethyl)-propionic acid were introduced into 30.0 parts of diethylene glycol dimethylether. A melt of 4.8 parts of trimethylolpropane and 4.5 parts of ethylene glycol was added dropwise over a period of 4 hours at 50° C. The reaction mixture was then stirred for 14 hours at 50° C. and a clear, colorless solution having a viscosity of 4500 mPa.s 23° C.) was obtained. The dissolved isocyanatocarboxylic acid had an isocyanate content of 12.9%, a carboxyl group content of 68 milliequivalents per 100 g, a monomeric diisocyanate I content of 0.4% and a monomeric hexamethylene diisocyanate content of 0.04%, based in each case on the solids content.

Example 13

53.4 parts of Diisocyanate I and 5.5 parts of 2,2-bis-(hydroxymethyl)-propionic acid were introduced into 30.0 parts of diethylene glycol dimethylether. 11.1 parts of 1,2,6-hexanetriol were added dropwise at 55° C. over a period of 2 hours. The reaction mixture was then stirred for 12 hours at 60° C. and for 8 hours at 80° C. The clear solution had a viscosity of 8700 mPa.s (23° C.). The dissolved isocyanatocarboxylic acid had an isocyanate content of 12.6%, a carboxyl group content of 59 milliequivalents per 100 g and a monomeric diisocyanate content of 0.9%, based in each case on the solids content.

Example 14

49.5 parts of Diisocyanate I and 3.4 parts of 2,2-bis-(hydroxymethyl)-propionic acid were introduced into 30.0 parts of diethylene glycol dimethylether. A molten mixture of 11.3 parts of trimethylolpropane and 5.8 parts of Polyether I was added dropwise over 3 hours at 50° C. The reaction mixture was then stirred for 15 hours at 50° C. and for 8 hours at 75° C. The clear solution had a viscosity of 9500 mPa.s (23° C.). The dissolved isocyanatocarboxylic acid had an isocyanate content of 11.9%, a carboxyl group content of 57 milliequivalents per 100 g and a monomeric diisocyanate content of 0.6%, based in each case on the solids content.

Example 15

56.1 parts of Diisocyanate II and 6.4 parts of 2,2-bis-hydroxymethyl)-propionic acid were introduced into 30.0 parts of diethylene glycol dimethylether. A molten mixture of 2.4 parts of ethylene glycol and 5.1 parts of trimethylolpropane was introduced dropwise at 60° C. over a period of 2 hours. A pale yellow solution having a viscosity of 7600 mPa.s (23° C.) was obtained after further stirring for 12 hours at 60° C. and for 8 hours at 80° C. The dissolved isocyanatocarboxylic acid had an isocyanate content of 9.9%, a carboxyl group content of 68 milliequivalents per 100 g and a monomeric diisocyanate content of 0.4%, based in each case on the solids content.

Example 16

55.0 parts of Diisocyanate II and 3.1 parts of 2,2-bis-(hydroxymethyl)-propionic acid were introduced into 30.0 parts of diethylene glycol dimethylether and heated to 60° C. A mixture of 9.3 parts of 1,2,6-hexanetriol and 2.6 parts of Polyether I was added dropwise at this temperature over a period of 3 hours. The reaction mixture was then stirred for 12 hours at that temperature, for 6 hours at 80° C. and for 1 hour at 100° C. The solution obtained had a viscosity of 1750 mPa.s (23° C.). The dissolved isocyanatocarboxylic acid had an isocyanate content of 12.0%, a carboxyl group content of 33 milliequivalents per 100 g and a monomeric diisocyanate content of 1.6%, based in each case on the solids content.

Example 17

50.7 parts of Diisocyanate II and 5.8 parts of 2,2-bis-(hydroxymethyl)-propionic acid were introduced into 35.0 parts of ethyl acetate. A mixture of 4.4 parts of 2,2,4-trimethyl-1,3-pentanediol and 4.1 parts of trimethylolpropane was added dropwise over a period of 2 hours at 55° C. The reaction mixture was then stirred for 14 hours at 60° C. and for 8 hours at 80° C. The solution obtained had a viscosity of 1100 mPa.s (23° C.). The dissolved isocyanatocarboxylic acid had an isocyanate content of 11.9%, a carboxyl group content of 66 milliequivalents per 100 g and a monomeric diisocyanate content of 1.9%, based in each case on the solids content.

Example 18 (Comparison Example)

51.5 parts of isophorone diisocyanate and 6.2 parts of 2,2-bis-(hydroxymethyl)-propionic acid were introduced into 35.0 parts of diethylene glycol dimethylether. 5.0 parts of trimethylolpropane and 2.3 parts of ethylene glycol were together introduced dropwise over a period of 4 hours at 50° C. The reaction mixture was then stirred at 100° C. for 12 hours. The clear product obtained had an isocyanate content of 7.5% and a monomeric diisocyanate content of 4.4%. The viscosity was 76,000 mPa.s (23° C.). After a storage time of over eight weeks at room temperature, the isocyanate content was 7.0% and the viscosity was 148,000 mPa.s (23° C.).

Examples for the dispersion of polyisocyanatocarboxylic acids

Example 19

21.5 parts of the product from Example 1 were finely ground and slowly stirred in this form into a mixture of 75 parts of water and 3.5 parts of dimethylethanolamine. A homogeneous, highly fluid dispersion with a blue tint was obtained after vigorous stirring for about 20 minutes. The suitability of the isocyanatocarboxylic acids dispersed in water as cross-linking agents for isocyanate-reactive binder components remained virtually unchanged for a period of about 6 hours.

Example 20

A mixture of 60.1 parts of water and 2.0 parts of dimethylethanolamine was added with vigorous stirring to 37.9 parts of the product from Example 2. A homogeneous white dispersion was obtained after about 5 minutes further stirring. The suitability of the isocyanatocarboxylic acids dispersed in water as cross-linking agents for isocyanate-reactive binder components remained virtually unchanged for a period of about 6 hours.

Example 21

A mixture of 47.4 parts of water and 2.3 parts of dimethylethanolamine was added with vigorous stirring to 50.3 parts of the polyisocyanatocarboxylic acid from Example 3. A finely divided, thin dispersion which had a slight bluish tint was obtained. This dispersion was stable for about 8 hours, i.e., it was only after this time that a noticeable reaction took place between the isocyanate groups and water, accompanied by the evolution of gas.

Example 22

48.3 parts of the polyisocyanatocarboxylic acid solution from Example 8 were introduced with vigorous stirring into a mixture of 50.5 parts of water and 1.2 parts of dimethylethanolamine. A finely divided dispersion which had a low viscosity and a slight bluish tint was obtained. The suitability of the isocyanatocarboxylic acids dispersed in water as cross-linking agents for isocyanate-reactive binder components remained virtually unchanged for a period of about 4 hours.

Example 23

A mixture of 57.6 parts of water and 0.9 parts of dimethylethanolamine was stirred into 41.5 parts of the product from Example 10. A relatively highly viscous dispersion was initially obtained but this changed after complete homogenization into a highly fluid dispersion having a pot life of about 4 hours.

Example 24

A mixture of 57.9 parts of water and 1.7 parts of dimethylethanolamine was introduced with vigorous stirring into 40.4 parts of the polyisocyanatocarboxylic acid solution from Example 12. A finely divided dispersion having a bluish tint and a processing time of about 3 hours was obtained.

Example 25

40.4 parts of the product from Example 13 were introduced into a reaction vessel. A mixture of 57.9 parts of water and 1.7 parts of dimethylethanolamine was added with vigorous stirring. A finely divided dispersion which remained virtually unchanged for about 6 hours was obtained after homogenization.

Example 26

A mixture of 54.7 parts of water and 1.5 parts of dimethylethanolamine was introduced with vigorous stirring into 43.8 parts of the product from Example 13. A low viscosity, finely divided dispersion with a slight bluish tint was obtained after homogenization. This dispersion remained virtually unchanged for several hours.

Example 27

A mixture of 57.4 parts of water and 1.0 part of dimethylethanolamine was stirred into 41.5 parts of the polyisocyanatocarboxylic acid from Example 14. After stirring for a brief period a homogeneous, finely divided, whitish dispersion was obtained. This dispersion remained virtually unchanged for several hours.

Example 28 (Comparison dispersion)

When attempts were made to disperse the product from Example 16 by a method analogous to that of Example 19, the product agglomerated with the evolution of gas.

Use

To demonstrate the use of the isocyanatocarboxylic acids according to the invention, the acids were used for cross-linking various hydroxyl group-containing aqueous polymer dispersions.

The cross-linking agents and polymer dispersions were combined as follows: The aqueous polymer dispersions were introduced into a reaction vessel and 1% by weight of a commercial wetting agent (Fluortensid FC 170 of 3M Company, Dusseldorf-Neuss, 10% solution in water) was added. The quantity of amine required for neutralizing the cross-linking agent and a further quantity of water were then added and the desired quantity of isocyanatocarboxylic acids according to the invention was stirred in. The resulting two-component aqueous coating compositions had a processing time of about 4 to 8 hours.

The coating compositions set forth in Table I were applied to glass plates by spray guns. They were dried at 140° C. for 20 minutes.

The solvent resistance was determined by leaving a cotton wool pad impregnated with solvent on the surface of the coating for 10 minutes and 1 minute (0=film unchanged, 5=film destroyed).

TABLE 1

| Example | 29 | 30 | 31 | 32 | 33 | 34 | 35 | 36 | 37 | 38 | 39 | 40 | 41 | 42 |
|---|---|---|---|---|---|---|---|---|---|---|---|---|---|---|
| OH dispersion | I | II | III | IV | II | IV | I | II | V | IV | VI | I | II | IV |
| Cross-linking Agent | 13 | 13 | 13 | 13 | 8 | 8 | 14 | 14 | 14 | 14 | 14 | 14 | 14 | 14 |
| NCO/OH ratio | 1.2 | 1.2 | 1.2 | 1.2 | 1.2 | 1.2 | 1.2 | 1.2 | 1.2 | 1.2 | 1.2 | 1.7 | 1.7 | 1.7 |
| Solids Content [%] | 25 | 35 | 37 | 33 | 35 | 31 | 30 | 33 | 33 | 33 | 33 | 35 | 42 | 35 |
| Solvent Content [%] | 12 | 21 | 4 | 45 | 10 | 3 | 13 | 11 | 5 | 7 | 5 | 11 | 15 | 9 |
| Xylene 10' | 0 | 0 | 0 | 0 | 0 | 0 | 1 | 0 | 1 | 0 | 1 | 0 | 0 | 0 |
| Xylene/BuAc 1'*) | 0 | 0 | 0 | 0 | 0 | 0 | 0 | 0 | 0 | 0 | 0 | 0 | 0 | 0 |
| MPA/Acetone 1'*) | 0 | 0 | 0 | 0 | 1 | 0 | 1 | 0 | 1 | 0 | 1 | 1 | 0 | 0 |
| Erichsen-cupping [mm] DIN 53 156 | 10.0 | 3.5 | 4.0 | 0.5 | 10.5 | 2.5 | 10.5 | 10.5 | 8.0 | 2.5 | 6.0 | 10.0 | 8.0 | 1.5 |
| Pendulum hardness [sec.] DIN 53 157 | 232 | 220 | 213 | 188 | 176 | 183 | 212 | 181 | 192 | 185 | 187 | 190 | 192 |  |

*)Ratio by weight: 1:1

To demonstrate the effectiveness of the isocyanatocarboxylic acids according to the invention for crosslinking aqueous polymer dispersions, the polymer dispersions were applied for comparison to glass plates, stored at 140° C. for 20 minutes (see Table 2) and subjected to the same tests, except that the Erichsen cupping was omitted due to the poor properties.

TABLE 2

| | (Comparison Examples) | | | | | |
|---|---|---|---|---|---|---|
| Examples | 43 | 44 | 45 | 46 | 47 | 48 |
| OH dispersion | I | II | III | IV | V | VI |
| Xylene 10' | 5 | 5 | 5 | 5 | 5 | 5 |
| Xylene/OuAc 1'* | 5 | 5 | 5 | 5 | 5 | 5 |
| MPA/Acetone 1'* | 5 | 5 | 5 | 5 | 5 | 5 |
| Pendulum hardness [sec] DIN 53 157 | sticky film | sticky film | 18 | 41 | sticky film | 76 |

*Ratio by weight: 1:1

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an isocyanato carboxylic acid containing
   a) 1 to 30% by weight of isocyanate groups attached to (cyclo)aliphatic tertiary carbon atoms and
   b) 0.5 to 500 milliequivalents, per 100 g of isocyanatocarboxylic acid, of carboxyl groups which may be at least partially present in carboxylate salt form, which comprises reacting at an NCO/OH equivalent ratio of 1.6:1 to 2:1
   A) a diisocyanate having a molecular weight of 168 to 300, an isocyanate group attached to a primary aliphatic carbon atom and an isocyanate group attached to a tertiary (cyclo)aliphatic carbon atom and
   B) up to 25 isocyanate equivalents percent, based on the equivalents of components A) and B), of one or more diisocyanates other than those set forth in A) which have a molecular weight of 168 to 300 and contain (cyclo)aliphatically bound isocyanate groups with
   C) 2,2-bis-(hydroxymethyl)-alkanoic acids corresponding to the formula

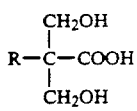

wherein
R represents hydrogen, a hydroxymethyl group or an alkyl group having 1 to 20 carbon atoms and
   D) optionally one or more organic polyhydroxyl compounds other than those set forth in C).

2. The process of claim 1 wherein component A) comprises a diisocyanate corresponding to the formula

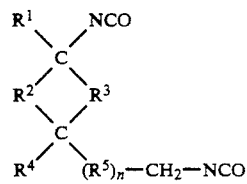

wherein
$R^1$ represents an alkyl group having 1 to 4 carbon atoms,
$R^2$ and $R^3$ represent the same or different divalent, saturated aliphatic hydrocarbon groups having 1 to 4 carbon atoms,
$R^4$ represents hydrogen or an alkyl group having 1 to 4 carbon atoms,
$R^5$ represents a divalent, saturated aliphatic hydrocarbon group having 1 to 4 carbon atoms and
n represents 0 or 1.

3. The process of claim 1 wherein component A) comprises 1-isocyanato-1-methyl-4(3)-isocyanatomethyl-cyclohexane, 1-isocyanato-1-methyl-4-(4-isocyanatobut-2yl))-cyclohexane and 1-isocyanato-1,2,2-trimethyl-3-(2-isocyanatoethyl)-cyclopentane.

4. The process of claim 1 wherein component C) comprises 2,2-bis-(hydroxymethyl)-propionic acid.

5. The process of claim 2 wherein component C) comprises 2,2-bis-(hydroxymethyl)-propionic acid.

6. The process of claim 3 wherein component C) comprises 2,2-bis-(hydroxymethyl)-propionic acid.

7. The process of claim 1 wherein said isocyanatocarboxylic acid contains less than 2% of unreacted, residual monomer without a separate step to remove unreacted monomer.

* * * * *